United States Patent
Baumann (10) Patent No.: US 9,279,777 B2
(45) Date of Patent: Mar. 8, 2016

(54) ANALYZING STRAIN DISTRIBUTION IN SEMICONDUCTOR STRUCTURES USING NANO-BEAM DIFFRACTION

(71) Applicant: International Business Machines Corporation, Armonk, NY (US)

(72) Inventor: Frieder H. Baumann, Red Bank, NJ (US)

(73) Assignee: International Business Machines Corporation, Armonk, NY (US)

(*) Notice: Subject to any disclaimer, the term of this patent is extended or adjusted under 35 U.S.C. 154(b) by 294 days.

(21) Appl. No.: 13/960,526

(22) Filed: Aug. 6, 2013

(65) Prior Publication Data

US 2015/0043802 A1 Feb. 12, 2015

(51) Int. Cl.
*G06T 7/00* (2006.01)
*G01N 23/205* (2006.01)

(52) U.S. Cl.
CPC .......... *G01N 23/2055* (2013.01); *G06T 7/0004* (2013.01); *G06T 2207/10061* (2013.01); *G06T 2207/30148* (2013.01)

(58) Field of Classification Search
CPC .................................................. G06T 7/0004
USPC ......................................................... 382/145
See application file for complete search history.

(56) References Cited

U.S. PATENT DOCUMENTS

| | | | |
|---|---|---|---|
| 6,144,443 A | 11/2000 | Ide | |
| 6,593,153 B2 | 7/2003 | Matsuda et al. | |
| 7,084,400 B2 | 8/2006 | Soeda | |
| 8,253,099 B2 | 8/2012 | Nicolopoulos et al. | |
| 2008/0078996 A1* | 4/2008 | Usuda | 257/48 |
| 2012/0146050 A1* | 6/2012 | Adam et al. | 257/77 |
| 2012/0274632 A1* | 11/2012 | Ivanov et al. | 345/419 |
| 2013/0206968 A1* | 8/2013 | Rouviere | 250/216 |
| 2015/0076346 A1* | 3/2015 | Weiss et al. | 250/307 |

* cited by examiner

*Primary Examiner* — Stephen R Koziol
*Assistant Examiner* — Delomia L Gilliard
(74) *Attorney, Agent, or Firm* — Steven J. Meyers; Hoffman Warnick LLC (57) ABSTRACT

Analyzing a strain distribution in a semiconductor structure. One embodiment includes a method including: determining a crystallographic orientation of a portion of the semiconductor structure depicted in a diffraction pattern image, identifying a first and a second diffraction spot in the diffraction pattern image, and detecting an anticipated location of each of a plurality of diffraction spots, based on the first and second diffraction spot, and the determining of the crystallographic orientation. The method includes forming perimeter tiles around the first and the second diffraction spot, and the anticipated location of each of the plurality of diffraction spots, and storing each of the formed perimeter tiles of the diffraction pattern image. Finally the method includes determining the strain distribution in the semiconductor structure based on an actual location of the first and the second diffraction spot, and each of the plurality of diffraction spots within the perimeter tile.

18 Claims, 6 Drawing Sheets

ANALYZING STRAIN DISTRIBUTION IN SEMICONDUCTOR STRUCTURES USING NANO-BEAM DIFFRACTION

BACKGROUND

1. Technical Field

The subject matter disclosed herein is related generally to analyzing a semiconductor structure. More particularly, the subject matter disclosed herein is related to analyzing a strain distribution in a semiconductor structure.

2. Related Art

During the manufacturing of conventional semiconductor structures a layer of the structure may be placed under a strain. The strain placed on the predetermined layer may create an increased mobility of the charge carriers of the semiconductor structure. That is, the strain may allow for greater and/or faster electrical connections within the semiconductor structure, which may ultimately increase the operational speed of the semiconductor structure. For example, during the manufacturing of a metal-oxide-semiconductor (MOS) structure, a layer of silicon (Si) may be placed under strain. In order to determine if the strain placed on the Si layer is operationally acceptable (e.g., meets predetermined manufacturing specifications) for the MOS structure, a strain distribution of the Si layer may be analyzed.

Conventionally, the strain distribution of a layer of a semiconductor may be measured using a variety of processes, including nano-beam diffraction (NBD). Conventional NBD is a transmission electron microscopy (TEM) technique which may examine strain in a layer of a semiconductor using a high-resolution diffraction pattern. Using NBD, a user may capture high-resolution diffraction patterns of different portions of the semiconductor structure including a strained layer. More specifically, the high-resolution images may include a diffraction pattern of the strained layer of the semiconductor structure. The high-resolution diffraction patterns typically are stored and later analyzed to determine the strain distribution within the strained layer of the semiconductor structure. However, in order to analyze an entire semiconductor structure, a plurality of high-resolution images of the portions of the semiconductor structure must be captured and stored. As a result of the large data size and number of high-resolution images used in a NBD process, a significant amount of storage space may be required for analyzing the strain distribution in a semiconductor structure.

BRIEF SUMMARY

A system for analyzing a strain distribution in a semiconductor structure is disclosed. One embodiment includes a method of analyzing a strain distribution in a semiconductor structure. The method includes: determining a crystallographic orientation of a portion of the semiconductor structure depicted in a diffraction pattern image; identifying a first diffraction spot and a second diffraction spot in the diffraction pattern image of the portion of the semiconductor structure; detecting an anticipated location of each of a plurality of diffraction spots in the diffraction pattern image, based on the identifying of the first diffraction spot, and the second diffraction spot, and the determining of the crystallographic orientation of the portion of the semiconductor structure; forming a perimeter tile around the first diffraction spot, the second diffraction spot and the anticipated location of each of the plurality of diffraction spots in the diffraction pattern image; storing each of the formed perimeter tiles of the diffraction pattern image; and determining the strain distribution in the semiconductor structure based on an actual location of the first diffraction spot, the second diffraction spot and each of the plurality of diffraction spots within the provided perimeter tile.

A first aspect of the invention includes a method of analyzing a strain distribution in a semiconductor structure. The method includes: determining a crystallographic orientation of a portion of the semiconductor structure depicted in a diffraction pattern image; identifying a first diffraction spot and a second diffraction spot in the diffraction pattern image of the portion of the semiconductor structure; detecting an anticipated location of each of a plurality of diffraction spots in the diffraction pattern image, based on the identifying of the first diffraction spot, and the second diffraction spot, and the determining of the crystallographic orientation of the portion of the semiconductor structure; forming a perimeter tile around the first diffraction spot, the second diffraction spot and the anticipated location of each of the plurality of diffraction spots in the diffraction pattern image; and determining the strain distribution in the semiconductor structure based on an actual location of the first diffraction spot, the second diffraction spot and each of the plurality of diffraction spots within the provided perimeter tile.

A second aspect of the invention includes a computer system having: at least one computing device configured to analyze a strain distribution in a semiconductor structure by performing actions including: determining a crystallographic orientation of a portion of the semiconductor structure depicted in a diffraction pattern image; identifying a first diffraction spot and a second diffraction spot in the diffraction pattern image of the portion of the semiconductor structure; detecting an anticipated location of each of a plurality of diffraction spots in the diffraction pattern image, based on the identifying of the first diffraction spot, and the second diffraction spot, and the determining of the crystallographic orientation of the portion of the semiconductor structure; forming a perimeter tile around the first diffraction spot, the second diffraction spot and the anticipated location of each of the plurality of diffraction spots in the diffraction pattern image; and determining the strain distribution in the semiconductor structure based on an actual location of the first diffraction spot, the second diffraction spot and each of the plurality of diffraction spots within the provided perimeter tile.

A third aspect of the invention includes a computer program product for analyzing a strain distribution in a semiconductor structure. The computer program product includes a computer readable storage medium having program code embodied therewith, the program code executable by at least one computer system to perform a method. The method includes: determining a crystallographic orientation of a portion of the semiconductor structure depicted in a diffraction pattern image; identifying a first diffraction spot and a second diffraction spot in the diffraction pattern image of the portion of the semiconductor structure; detecting an anticipated location of each of a plurality of diffraction spots in the diffraction pattern image, based on the identifying of the first diffraction spot, and the second diffraction spot, and the determining of the crystallographic orientation of the portion of the semiconductor structure; providing a perimeter tile around the first diffraction spot, the second diffraction spot and the anticipated location of each of the plurality of diffraction spots in the diffraction pattern image; and determining the strain distribution in the semiconductor structure based on an actual location of the first diffraction spot, the second diffraction spot and each of the plurality of diffraction spots within the provided perimeter tile.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

As described herein, aspects of the invention relate to analyzing a semiconductor structure. Specifically, as described herein, aspects of the invention relate to analyzing a strain distribution in a semiconductor structure.

Figure 1:
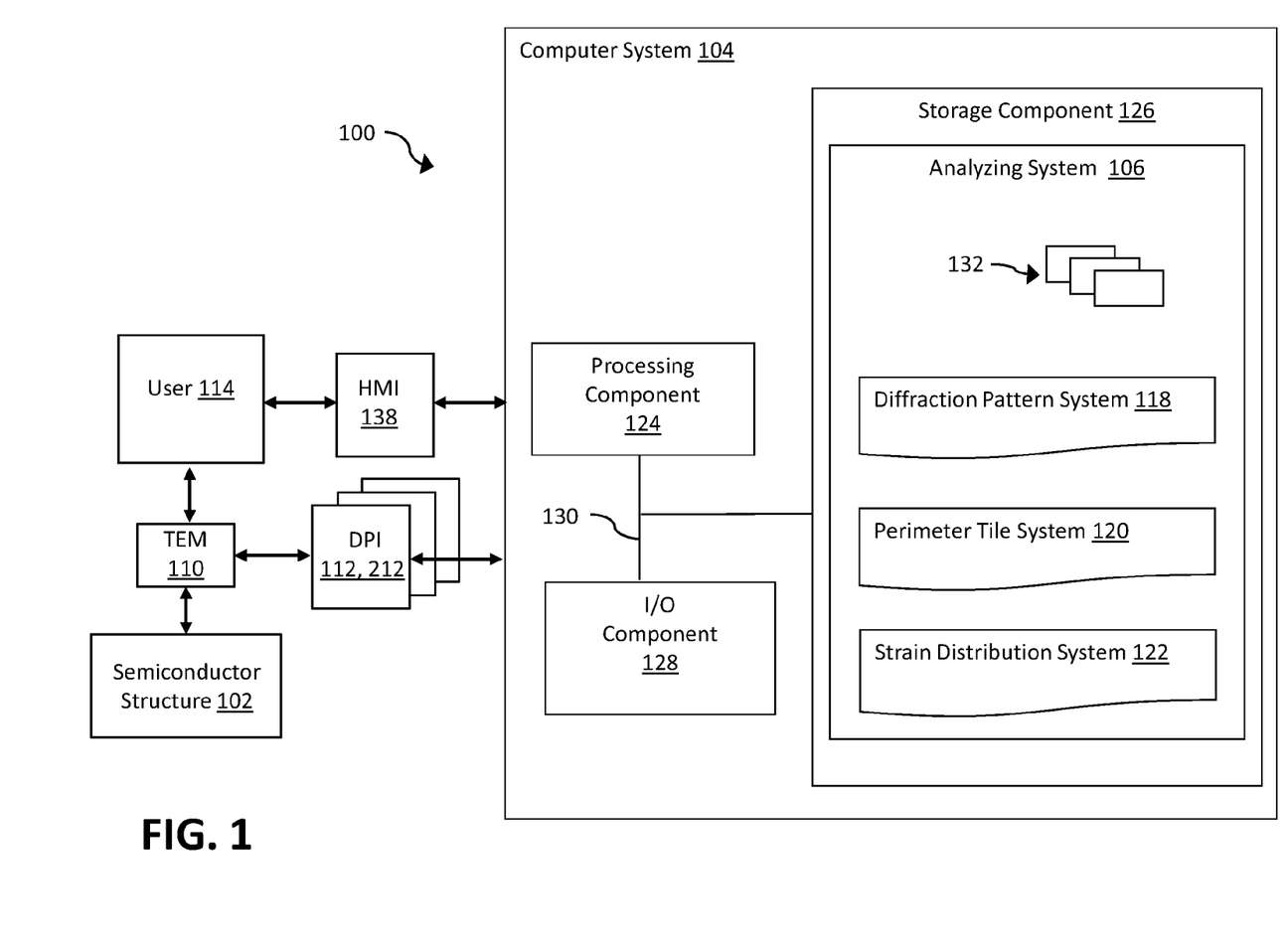
FIG. 1 shows a demonstrative illustration of an environment for analyzing a strain distribution of a semiconductor structure according to embodiments of the invention.

Turning to FIG. 1, a demonstrative illustration of an environment 100 for analyzing a strain distribution in a semiconductor structure 102 is shown according to embodiments. To this extent, the environment 100 includes a computer system 104 that can perform processes described herein in order to analyze a strain distribution in semiconductor structure 102. In particular, the computer system 104 is shown as including a analyzing system 106, which makes computer system 104 operable to analyzing a strain distribution in a semiconductor structure 102 by performing any/all of the processes described herein and implementing any/all of the embodiments described herein.

As shown in FIG. 1, environment 100 may include semiconductor structure 102. Semiconductor structure 102 may include a metal-oxide-semiconductor (MOS) including a silicon layer 108 (FIGS. 3-9) that may undergo a straining process during the manufacturing of MOS structure (e.g., semiconductor structure 102). However, it is understood that semiconductor structure 102 may not be limited to MOS structures, and may include any conventional semiconductor structure that may undergo a straining process during manufacturing. Additionally, it is understood that the layer of semiconductor structure 102 undergoing the straining process during manufacturing may include any conventional layer of semiconductor structure 102 that may undergo a straining process during manufacturing.

In a demonstrative illustration, as shown in FIG. 1, environment 100 may also include a transmission electron microscope (TEM) 110. TEM 110 may capture a plurality of distinct images of semiconductor structure 102 including images (not shown) of portions of the semiconductor structure 102 and images of a diffraction pattern (DPI) 112 of portions of semiconductor structure 102. More specifically, a user 114 (e.g., semiconductor technician) may utilize TEM 110 to capture the plurality of diffraction pattern images 112 of a portion of semiconductor structure 102 after a straining process has been performed on the semiconductor structure 102. The plurality of diffraction pattern images 112 may be a graphical or visual representation of the diffraction pattern of silicon layer 108 (FIG. 3-9) of semiconductor structure 102, captured and/or generated by TEM 110. As discussed herein, diffraction pattern images 112 may be used in analyzing strain distribution in silicon layer 108 (FIG. 3-9) of semiconductor structure 102. TEM 110 may include any now known or later developed transmission electron microscope capable of capturing and/or generating a plurality of images (e.g., images of silicon layer 108 (not shown), diffraction pattern images 112) of semiconductor structure 102. The plurality of diffraction pattern images 112 may include a digital image of distinct portions of the semiconductor structure 102. More specifically, each of the plurality of diffraction pattern images 112 may include a digital image of a diffraction pattern for a distinct portion of semiconductor structure 102, such that all of the plurality of diffraction pattern images 112 combined shows the entire semiconductor structure 102. As discussed herein, the process of analyzing the strain distribution of semiconductor structure 102 using a single diffraction pattern image 112 may be repeated on all of the plurality of diffraction pattern images 112 captured by TEM 110. As such, computer system 104 may analyze the strain distribution of the entire semiconductor structure 102 using the plurality of diffraction pattern images 112.

Figure 3:
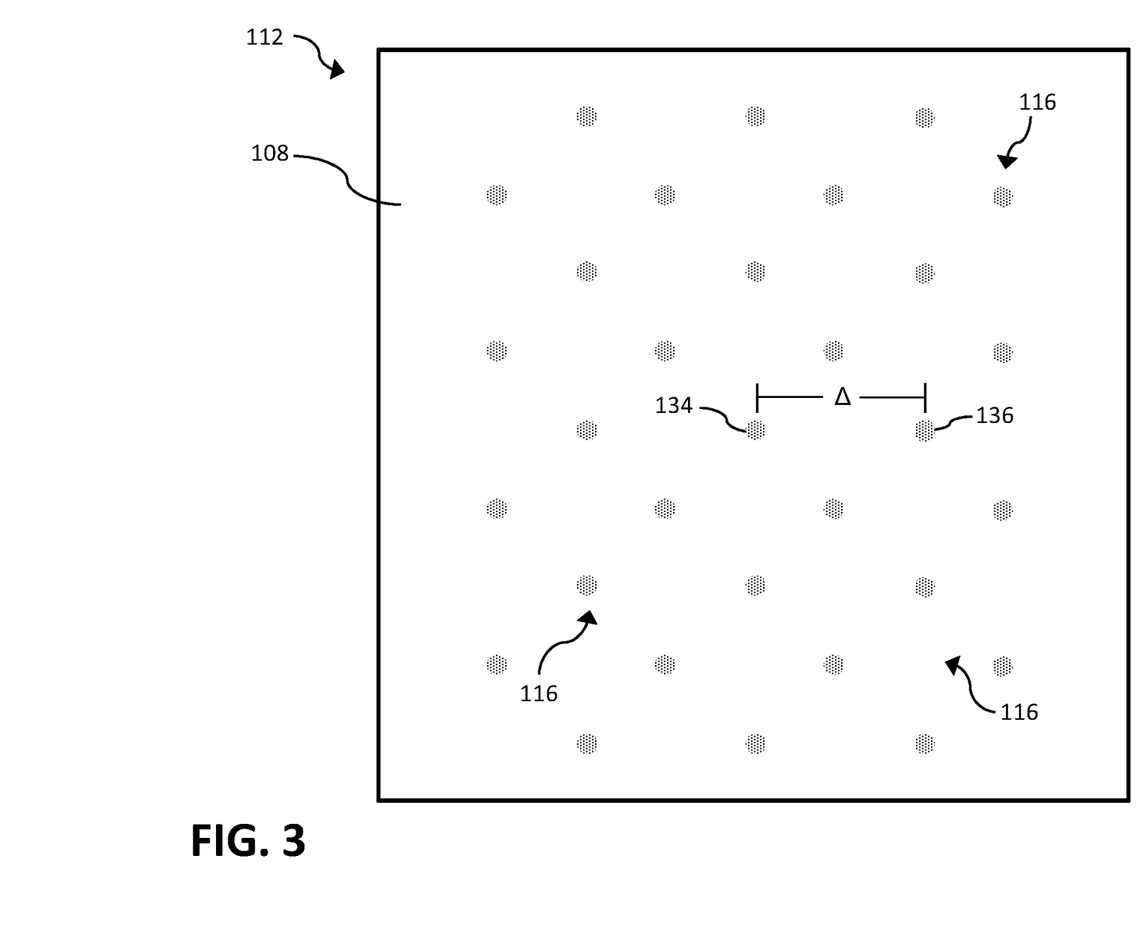
FIGS. 3-5 show a demonstrative illustration of a diffraction pattern of a portion of a semiconductor structure undergoing a method of analyzing a strain distribution in the semiconductor structure according to embodiments of the invention.

Briefly turning to FIG. 3, a demonstrative illustration of a diffraction pattern image 112 of a portion of a semiconductor structure 102 (FIG. 1) is shown according to embodiments of the invention. Diffraction pattern image 112, as shown in FIG. 3, may include a distinct diffraction pattern image of the plurality of diffraction pattern images 112 captured using TEM 110 (FIG. 1). As shown in FIG. 3, diffraction pattern image 112 may include a plurality of diffraction spots 116. The plurality of diffraction spots 116 may be formed in silicon layer 108 after a conventional straining process is performed on semiconductor structure 102 (FIG. 1). As shown in FIG. 3, the plurality of diffraction spots 116 may be configured as a plurality of substantially circular dots in diffraction pattern image 112. However, it is understood that the plurality of diffraction spots 116 of diffraction pattern image 102 may include any conventional configuration that may identify a diffraction spot 116 in a portion of silicon layer 108 of semiconductor structure 102 (FIG. 1).

Returning to FIG. 1, analyzing system 106 may include a diffraction pattern system 118, a perimeter tile system 120, and a strain distribution system 122, for allowing computer system 104 to analyze a strain distribution in semiconductor structure 102. As discussed herein, each of the distinct systems (e.g., diffraction pattern system 118, perimeter tile system 120, strain distribution system 122) of analyzing system 106 may perform at least one process in order to allow computer system 104 to analyze a strain distribution in semiconductor structure 102.

The computer system 104 is shown including a processing component 124 (e.g., one or more processors), a storage component 126 (e.g., a storage hierarchy), an input/output (I/O) component 128 (e.g., one or more I/O interfaces and/or devices), and a communications pathway 130. In general, the processing component 124 executes program code, such as the analyzing system 106, which is at least partially fixed in the storage component 126. While executing program code, the processing component 124 can process data, which can result in reading and/or writing transformed data from/to the storage component 126 and/or the I/O component 128 for further processing. The pathway 130 provides a communications link between each of the components in the computer system 104. The I/O component 128 can comprise one or more human I/O devices, which enable a system user 114 (e.g., a technician) to interact with the computer system 104 and/or one or more communications devices to enable a system user 114 to communicate with the computer system 104 using any type of communications link. To this extent, the analyzing system 106 can manage a set of interfaces (e.g., graphical user interface(s), application program interface, etc.) that enable human and/or system users 114 to interact with the analyzing system 106. Further, the analyzing system 106 can manage (e.g., store, retrieve, create, manipulate, organize, present, etc.) data using any solution. More specifically, analyzing system 102 can store the plurality of diffraction pattern images 112 in storage component 126 as described herein.

In any event, the computer system 104 can comprise one or more general purpose computing articles of manufacture (e.g., computing devices) capable of executing program code, such as the analyzing system 106, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analyzing system 106 can be embodied as any combination of system software and/or application software.

Further, the analyzing system 106 can be implemented using a set of modules 132. In this case, a module 132 can enable the computer system 104 to perform a set of tasks used by the analyzing system 106, and can be separately developed and/or implemented apart from other portions of the analyzing system 106. As used herein, the term "component" means any configuration of hardware, with or without software, which implements the functionality described in conjunction therewith using any solution, while the term "module" means program code that enables the computer system 104 to implement the functionality described in conjunction therewith using any solution. When fixed in a storage component 126 of a computer system 104 that includes a processing component 124, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 104.

When the computer system 104 comprises multiple computing devices, each computing device may have only a portion of analyzing system 106 fixed thereon (e.g., one or more modules 132). However, it is understood that the computer system 104 and analyzing system 106 are only representative of various possible equivalent computer systems that may perform a process described herein. To this extent, in other embodiments, the functionality provided by the computer system 104 and analyzing system 106 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 104 includes multiple computing devices, the computing devices can communicate over any type of communications link. Further, while performing a process described herein, the computer system 104 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

While shown and described herein as a method and computer system for analyzing a strain distribution in semiconductor structure 102, it is understood that aspects of the invention further provide various alternative embodiments. For example, in one demonstrative illustration, the invention provides a computer program fixed in at least one computer-readable medium, which when executed, enables a computer system to analyze a strain distribution in a semiconductor structure. To this extent, the computer-readable medium includes program code, such as the analyzing system 106, which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another demonstrative illustration, the invention provides a method of providing a copy of program code, such as the analyzing system 106 (FIG. 1), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, a demonstrative illustration of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another demonstrative illustration, the invention provides a method of analyzing a strain distribution in semiconductor structure 102. In this case, a computer system, such as the computer system 104 (FIG. 1), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

Figure 2:
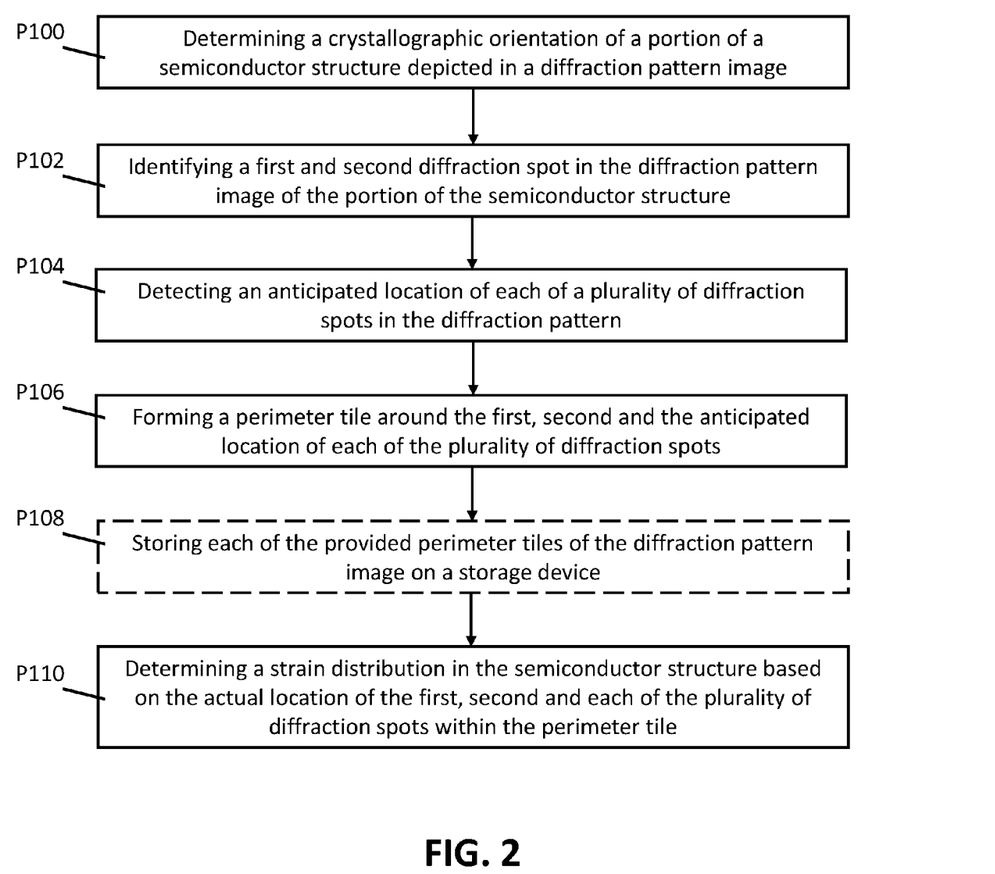
FIG. 2 shows a demonstrative illustration of a method flow diagram illustrating processes in a method of analyzing a strain distribution in a semiconductor structure according to embodiments of the invention.

FIG. 2 is a demonstrative illustration of a method flow diagram illustrating processes in a method of analyzing a strain distribution in semiconductor structure 102 according to embodiments of the invention. The method flow diagram illustration in FIG. 2 will be referred to in conjunction with FIGS. 1 and 3-6, and in particular, FIG. 1, which illustrates environment 100 for performing the processes described with reference to method flow diagram of FIG. 2. As shown, one method can include the following processes:

With reference to FIG. 1, a preliminary process (not shown) may first be performed during the analyzing of a strain distribution of semiconductor structure 102. Specifically, the preliminary process (not shown) may include: obtaining the plurality of diffraction pattern images 112 of semiconductor structure 102 on computer system 104. More specifically, user 114 may capture the plurality of diffraction pattern images 112 using TEM 110, and may transmits the plurality of diffraction pattern images 112 to computer system 104. User 114 may transmit the plurality of diffraction pattern images 112 to computer system 104 by any conventional data transfer technique, for example, but not limited to, directly from TEM 110 or an intermediate storage system.

After the preliminary process (not shown) process P100, as shown in FIG. 2, can include: determining a crystallographic orientation of a portion of semiconductor structure 102 depicted in diffraction pattern image 112. More specifically, as shown in FIG. 3, the positioning of the plurality of diffraction spot 116 in diffraction pattern image 112 may be observed by user 114 using computer system 104 (FIG. 1) to determine the crystallographic orientation of the portion of semiconductor structure 102 depicted in diffraction pattern image 112. That is, depending on the orientation of the plurality of diffraction spot 116 in silicon layer 108 of semiconductor structure 102 (FIG. 1), the crystallographic orientation of semiconductor structure 102 may be determined. The crystallographic orientation of semiconductor structure 102 may include the orientation of semiconductor structure 102 and/or the direction in which the electron beam of TEM 110 may be directed toward semiconductor structure 102 when capturing and/or generating the plurality of diffraction pattern images 112. As shown in FIG. 3, it may be determined that the crystallographic orientation of semiconductor structure 102 is a 110 orientation. That is, as shown in FIG. 3, the crystallographic orientation of semiconductor structure 102 is such that an electron beam of TEM 110 (FIG. 1) may be directed toward a diagonal face or surface of semiconductor structure 102. As such, and as shown in FIG. 3, the plurality of diffraction spots 116 depicted in diffraction pattern image 112 are substantially diagonal from row-to-row of the plurality of diffraction spots 116. In an alternative demonstrative illustrations (not shown), where the rows and columns of the plurality of diffraction spots 116 shown in the diffraction pattern image 112 are substantially aligned, it may be determined that the semiconductor structure 102 may be in a 100 orientation (e.g., electron beam directed toward an edge of semiconductor structure 102). Additionally, the crystallographic orientation of semiconductor structure 102 may be determined prior to directing an electron beam of TEM 110 (FIG. 1) through semiconductor structure 102. That is, user 114 (FIG. 1) utilizing TEM 110 may initially determine the crystallographic orientation of semiconductor structure 102 prior to directing a electron beam through semiconductor 102 and subsequently capturing and/or generating the plurality of diffraction pattern images 112, as discussed herein.

Following process P100, process P102, as shown in FIG. 2 can include: identifying a first diffraction spot 134 and a second diffraction spot 136 in diffraction pattern image 112 (FIG. 3) of the portion of semiconductor structure 102 (FIG. 1). More specifically, as shown in FIG. 3, diffraction pattern image 112 may be examined and first diffraction spot 134 and second diffraction spot 136 of a single diffraction pattern image 112 may be identified. With reference to FIGS. 1 and 3, first diffraction spot 134 and second diffraction spot 136 of diffraction pattern image 112 (FIG. 3) may be identified by any conventional searching technique now known or later developed. That is, as discussed herein, first diffraction spot 134 of diffraction pattern image 112 may be identified as a distinct diffraction spot of the plurality of diffraction spot 116 positioned substantially in the center of diffraction pattern image 112, and second diffraction spot 136 may then be subsequently identified as a diffraction spot positioned adjacent first diffraction spot 134. For example, once diffraction pattern image 112 is captured, a user 114 (FIG. 1) may view diffraction pattern image 112 and may substantially identify first diffraction spot 134 and second diffraction spot 136 via a user input. More specifically, user 114 may view diffraction pattern image 112 using a human-machine interface (HMI) 138, and may visually identify first diffraction spot 134 and second diffraction spot 136 of diffraction pattern image 112. HMI 138 may include, but is not limited to an interface, such as a graphical user interface (GUI) or other conventional interface, for providing user 114 with an interactive visual of diffraction pattern image 112. In a further example, as shown in FIGS. 1 and 3, user 114 may engage diffraction pattern system 118 (FIG. 1) to examine diffraction pattern image 112 in order to identify first diffraction spot 134 and second diffraction spot 136 in diffraction pattern image 112 (FIG. 3). Diffraction pattern system 118 may include any conventional processing component (e.g., computer program) configured, at least in part, to inspect, analyze and identify first diffraction spot 134 and second diffraction spot 136 in diffraction pattern image 112.

The identifying of first diffraction spot 134 and second diffraction spot 136 of diffraction pattern image 112 may also include determining a spatial difference ($\Delta$) between first diffraction spot 134 and second diffraction spot 136. More specifically, the identifying may include first determining a location of first diffraction spot 134 and subsequently determining a location of second diffraction spot 136. The location of first diffraction spot 134 and second diffraction spot 136 may be determined by diffraction pattern system 118 of analyzing system 106, as shown in FIG. 1. That is, user 114 may view diffraction pattern image 112 using a human-machine interface (HMI) 138, and may utilize HMI 138 to identify first diffraction spot 134 and second diffraction spot 136. Once user 114 identifies first diffraction spot 134 and second diffraction spot 136, diffraction pattern system 118 may obtain the identified first diffraction spot 134 and second diffraction spot 136, and determine the spatial difference ($\Delta$) between first diffraction spot 134 and second diffraction spot 136. Diffraction pattern system 118 of analyzing system 106 may determine the spatial difference ($\Delta$) between first diffraction spot 134 and second diffraction spot 136 by any conventional technique including, but not limited to: first determining the actual dimension of the portion of semiconductor structure 102 illustrated in diffraction pattern image 112, and subsequently determining the spatial difference based on the determined actual dimensions and the identified position of first diffraction spot 134 and second diffraction spot 136. As discussed herein, the determined spatial difference ($\Delta$) between first diffraction spot 134 and second diffraction spot 136 may be used in subsequent processes.

Turning to FIG. 3, the plurality of diffraction spot 116 formed in silicon layer 108 may include first diffraction spot 134 and second diffraction spot 136. First diffraction spot 134 may be located substantially in the center of diffraction pattern image 112 and second diffraction spot 136 may be positioned substantially proximate first diffraction spot 134. More specifically, first diffraction spot 134 may be a substantial origin of the plurality of diffraction sport 116, and second diffraction spot 136 may be located directly adjacent and substantially in the same row of the plurality of diffraction spots 116 as first diffraction spot 134. However, it is understood that second diffraction spot 136 may be any single diffraction spot of the plurality of diffraction spots 116 that may be directly adjacent to first diffraction spot 134, without a distinct diffraction spot 116 positioned between first diffraction spot 134 and second diffraction spot 136. As shown in FIGS. 1 and 3, first diffraction spot 134 and second diffraction spot 136 in diffraction pattern image 112 may be identified by user 114 (FIG. 1). More specifically, user 114 may utilize HMI 138 (FIG. 1) to view diffraction pattern image 112, as shown in FIG. 3, and examine the plurality of diffraction spots 116 in silicon layer 108. Additionally, user 114 may identify first diffraction spot 134 positioned substantially in the center of diffraction pattern image 112 and second diffraction spot 136 positioned adjacent first diffraction spot 134. User 114 may also transmit the position of first diffraction spot 134 and second diffraction spot 136 in diffraction pattern image 112 to diffraction pattern system 118 of analyzing system 106 using HMI 138. Diffraction pattern system 118 of analyzing system 106 may receive the position of first diffraction spot 134 and second diffraction spot 136 in diffraction pattern image 112, and may subsequently determine the spatial difference ($\Delta$) between first diffraction spot 134 and second diffraction spot 136.

Following process P102, process P104 may include: detecting an anticipated location 140 (shown in phantom) of each of the plurality of diffraction spots 116 in diffraction pattern image 112, based on the identifying of first diffraction spot 134, and second diffraction spot 136, and the determining of the crystallographic orientation of the portion of semiconductor structure 102. That is, with reference to FIGS. 1 and 4, diffraction pattern system 118 of analyzing system 106 (FIG. 1) may detect anticipated location 140 of each of the plurality of diffraction spots 116 in diffraction pattern image 112 based on the position of first diffraction spot 134, second diffraction spot 136 identified by user 114 and/or diffraction pattern system 118 (FIG. 1), and the determined crystallographic orientation of semiconductor structure 102. The detecting of anticipated location 140 of each of the plurality of diffraction spots 116 may include identifying a locational pattern 142 of the plurality of diffraction spots 116. The locational pattern 142 may be based upon, at least in part, the determined crystallographic orientation of the portion of semiconductor structure 102, and the spatial difference ($\Delta$) between first diffraction spot 134 and second diffraction spot 136. More specifically, diffraction pattern system 118 may identify locational pattern 142 including anticipated location 140 of each of the plurality of diffraction spots 116, where the location pattern 142 is substantially identical to the pattern of the plurality of diffraction spots 116 identified by determining the crystallographic orientation of semiconductor structure 102. Additionally, diffraction pattern system 118 may identify locational pattern 142 including anticipated location 140 of each of the plurality of diffraction spots 116, where each anticipated location 140 is spaced apart a distance equal to the determined spatial difference ($\Delta$) between first diffraction spot 134 and second diffraction spot 136. Locational pattern 142, including anticipated location 140 of each of the plurality of diffraction spots 116, may represent a preferred pattern for the diffraction spots 116 of semiconductor structure 102 that has been uniformly strained (e.g., no displacement of the diffraction spots116) during a manufacturing process. Where uniform strain is achieved on silicon layer 108, semiconductor structure 102 may operate with a desired function and/or high efficiency.

Figure 4:
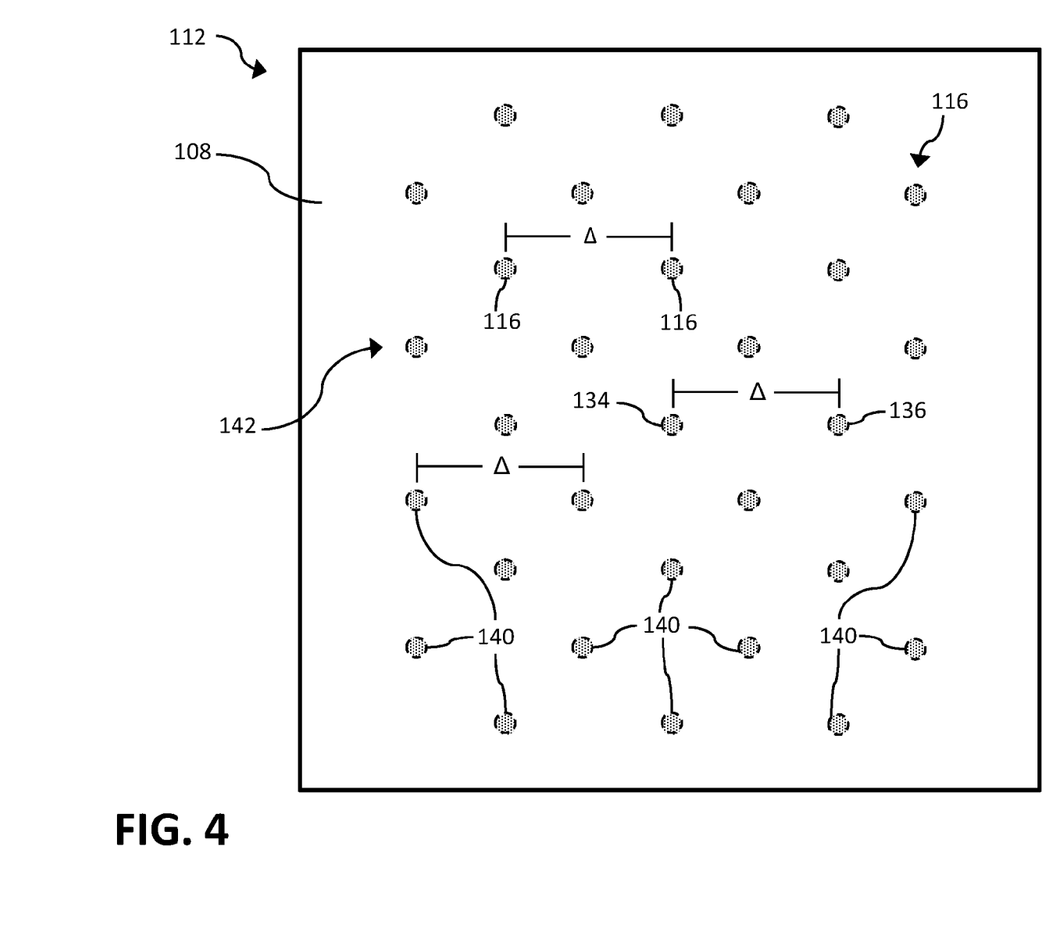

Continuing the example of process P102, in process P104 diffraction pattern system 118 of analyzing system 106 may detect anticipated location 140 (shown in phantom) of each of the plurality of diffraction spots 116 based on the identified first diffraction spot 134 and second diffraction spot 136, and the determined crystallographic orientation of semiconductor structure 102. For example, the demonstrative illustration shown in FIG. 4 may show a demonstrative illustration of a diffraction pattern image 112 illustrating locational pattern 142 including anticipated location 140 of each of the plurality of diffraction spots 116. That is, by identifying first diffraction spot 134 and second diffraction spot 136, and determining the crystallographic orientation of semiconductor structure 102 is a 110 orientation (e.g., diffraction spots 116 substantially diagonal from row-to-row), anticipated locations 140 may be detected and location pattern 142 may be generated. Diffraction pattern image 112, as shown in FIG. 4, may be displayed to user 114 via HMI 138 (FIG. 1). In the example, as shown in FIG. 4, diffraction spots 116 of diffraction pattern image 112 may be positioned in a preferred pattern or location of semiconductor structure 102 (FIG. 1). That is, in the example as shown in FIG. 4, the plurality of diffraction spots 116 may not be substantially displaced by a localized, undesirable strain placed on silicon layer 108 of semiconductor structure 102 (FIG. 1), as discussed herein. As a result, each of anticipated locations 140 detected on diffraction pattern image 112 may be in substantial alignment with the actual plurality of diffraction spots 116 (e.g., diffraction spots 146, 148) positioned in silicon layer 108.

Figure 5:
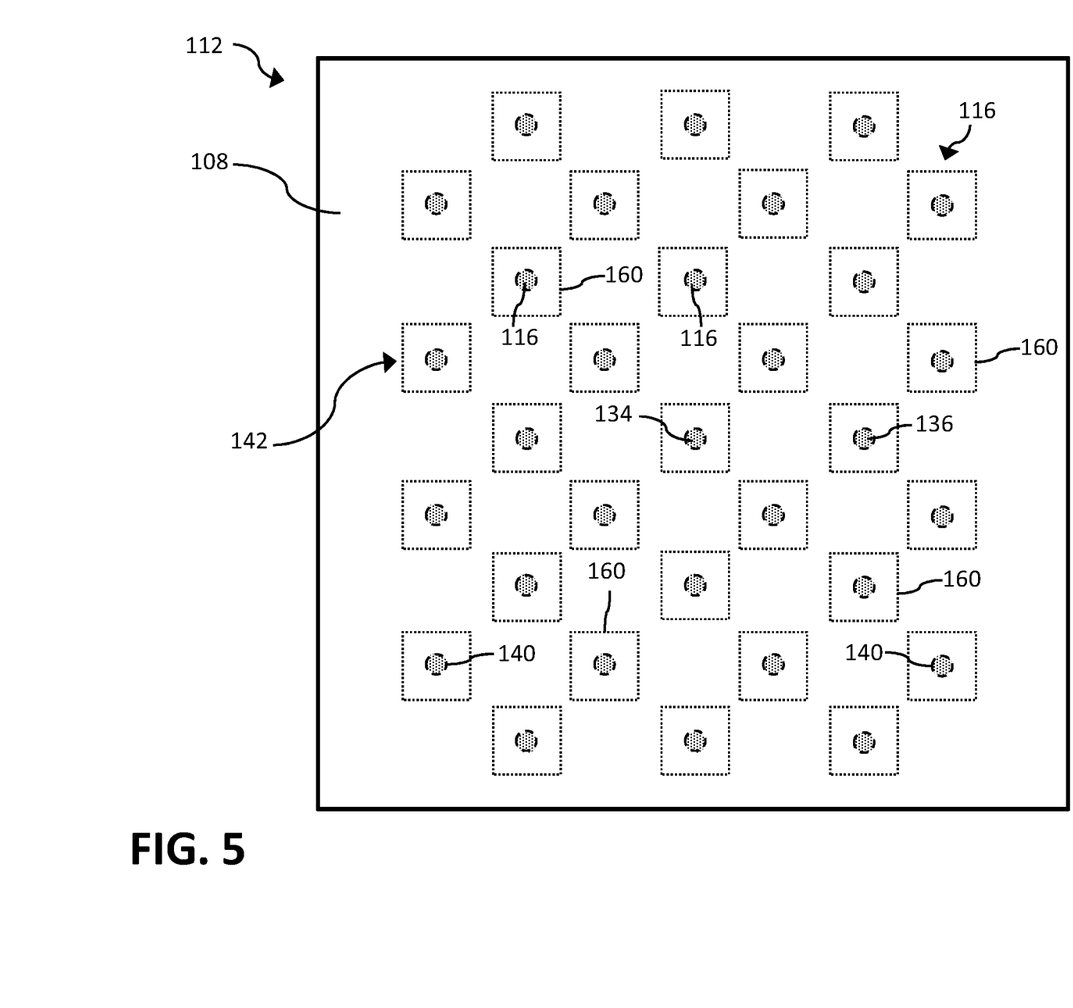

After the detecting anticipated locations 140 in process P104, process P106 can include forming a perimeter tile 160 around first diffraction spot 134, second diffraction spot 136 and anticipated location 140 of each of the plurality of diffraction spots 116 in diffraction pattern image 112. More specifically, in process P106, perimeter tile system 120 of analyzing system 106 (FIG. 1) may generate a plurality of perimeter tiles 160 on diffraction pattern image 112 (FIG. 5), where each individual perimeter tile 160 may substantially surrounds a single diffraction spot 116 (e.g., first diffraction spot 134, second diffraction spot 136) and/or anticipated location 140 of each of the plurality of diffraction spots 116. Perimeter tiles 160 may be generated such that the center of each perimeter tile 160 may be substantially aligned with the center of each anticipated location 140 of each of the plurality of diffraction spots 116. In a demonstrative illustration, as shown in FIG. 5, perimeter tiles 160 include an area in a spatial range of about 0.5% and about 2.5% of anticipated location 140 of each of the plurality of diffraction spots 116. That is, perimeter tile system 120 of analyzing system 106 may generate perimeter tiles 160 having an area at least about 0.5% to about 2.5% larger than the area of anticipated location 140. The area of perimeter tiles 160 generated by perimeter tile system 120 of analyzing system 106 may be dependent on, at least in part, predetermined characteristics of semiconductor structure 102 (FIG. 1) including, but not limited to: the material composition of semiconductor structure 102, the size of semiconductor structure 102, the characteristics of the straining process bring performed on semiconductor structure 102, etc. The area of perimeter tiles 160 generated by perimeter tile system 120 may also be dependent on, at least in part, that the actual location of each of the plurality of diffraction spots 116 being within a spatial range of about 0% to about 2% of anticipated location 140 of each of the plurality of diffraction spots 116. More specifically, as a result of a straining process being performed on semiconductor structure 102 (FIG. 1), the strain distribution in semiconductor structure 102 may not displace diffraction spots 116 in silicon layer 108 substantially more than 2% from a desired location (e.g., anticipated location 140). However, if diffraction spots 116 in silicon layer 108 were displaced more than 2%, semiconductor structure 102 (FIG. 1) may include an undesirable, defective circuit area (e.g., shorted circuit area), which may not allow semiconductor structure 102 to function properly. As shown in FIG. 5, perimeter tiles 160 may be substantially polygonal. However, it is understood that perimeter tiles 160 may be generated as any conventionally shape (e.g., circle) that may substantially surround the plurality of diffraction spots 116 and/or anticipated location 140 of each of the plurality of diffraction spots 116. As discussed herein, perimeter tiles 160 may form a search area for computer system 104 (FIG. 1) for determining the displacement of the plurality of diffraction spots 116 in silicon layer 108, and which may subsequently aid in determining a strain distribution in semiconductor structure 102.

Continuing the example from process P104, in process P106, perimeter tile system 120 of analyzing system 106 may form perimeter tiles 160 having an area about 1.5% larger than the area of anticipated location 140. More specifically, as shown in FIG. 5, perimeter tile system 120 (FIG. 1) may form perimeter tiles 160 to include an area 1.5% larger than the area of anticipated location 140 as a result of strained layer of semiconductor structure 102 (FIG. 1) being silicon layer 108, and specific, conventional straining process silicon layer 108 of semiconductor structure may undergo. As a result of perimeter tiles 160 including an area 1.5% larger than the area of anticipated location 140, it may be understood that any of the plurality of diffraction patterns 116 positioned outside of perimeter tiles 160 may indicate an undesirable, defective circuit area in semiconductor structure 102. That is, an area 1.5% larger than the area of anticipated location 140 may be the maximum allowed displacement of diffraction spots 116, and any further displacement of diffraction spots 116 in silicon layer 108 may result in defective circuit areas in semiconductor structure 102. As shown in FIG. 5, diffraction spots 116 may all be positioned within the respective anticipated locations 140 and perimeter tiles 160. As discussed herein, the positioning of diffraction spots 116 within the area of perimeter tile 160 may indicate a substantially uniform or desirable strain was achieved on silicon layer 108 of semiconductor structure 102 during the straining process.

Following process P106, an optional process P108 (shown in phantom) may include storing each of the formed perimeter tiles 160 of the diffraction pattern image 112 on a storage device (e.g., storage component 126 (FIG. 1)). The storing of each of the provided perimeter tiles 160 may be stored separate from storing the entire diffraction pattern image 112 of the portion of semiconductor structure 102 (FIG. 1). That is, rather than storing each of the plurality of diffraction pattern images 112 captured by TEM 110 within computer system 104 (FIG. 1), each perimeter tile 160 surrounding a single diffraction spot 116 (e.g., first diffraction spot 134, second diffraction spot 136) and/or anticipated location 140 of each of the plurality of diffraction spots 116 may be stored instead. Storing each of the formed perimeter tiles 160 may include storing the contents found within the area of perimeter tile 106 (e.g., plurality of diffraction spots 116, anticipated location 140), and also storing the location of the perimeter tile 160 within diffraction pattern images 112. As discussed herein, the content found within the area of perimeter tile 106 may be used to determining the actual location of the plurality of diffraction spots 116 and/or determining the center of each of the plurality of diffraction spots 116. The process of storing each of the formed perimeter tiles 160 of the diffraction pattern image 112 may substantially reduce the file size saved on computer system 104. That is, by only storing the formed perimeter tiles 160 in storage component 126 of computer system 104, the storage space required by computer system 104 for utilizing diffraction pattern image 112 to analyze the strain distribution in semiconductor structure 102 is substantially reduced. As a result, the strain distribution in a plurality of semiconductor structures 102 may be analyzed using computer system 104 without requiring additional storage space in storage component 126. Although discussed as following process P106, it is understood that optional process P108 may also be performed after process P110, as discussed herein.

After performing process P106, and potentially performing optional process P108, process P110 can include determining the strain distribution (FIG. 6) in semiconductor structure 102 based on an actual location of first diffraction spot 134, second diffraction spot 136 and each of the plurality of diffraction spots 116 within the formed perimeter tile 160. That is, with reference to FIGS. 1, 5 and 9, strain distribution system 122 of computer system 104 (FIG. 1) may determine the strain distribution (FIG. 6) in semiconductor structure 102 by determining the actual location of each diffraction spot 116 within each corresponding perimeter tile 160 and/or anticipated location 140 of diffraction spot 116. More specifically, the determining in process P110 may include determining the spatial distance (D)(FIG. 6) between anticipated location 140 of each of the plurality of diffraction spots 116 and the actual location of each of the plurality of diffraction spots 116. That is, strain distribution system 122 may analyze each individual perimeter tile 160 including anticipated location 140 and diffraction spot 116 to determine which perimeter tiles 160 includes a spatial distance (D) between anticipated location 140 and the actual location of a diffraction spot 116 in perimeter tile 160 (e.g., FIG. 6). After strain distribution system 122 of computer system 104 determines the spatial distance (D) between anticipated location 140 and the actual location of a diffraction spot 116 in perimeter tile 160, strain distribution system 122 may identify an approximate location of a strain force (FIG. 6) of silicon layer 108 of semiconductor structure 102. That is, depending on strain distribution system 122 determining which perimeter tiles 160 include a spatial distance (D) between anticipated location 140 and the actual location of a diffraction spot 116, strain distribution system 122 may approximate where strain force may be in silicon layer 108 that may cause strain distribution (FIG. 6) in semiconductor structure 102.

Additionally, the determining of strain distribution (FIG. 6) may also include determining a direction of strain distribution in semiconductor structure 102. That is, in determining the spatial distance (D) between anticipated location 140 and the actual location of a diffraction spot 116 in perimeter tile 160, strain distribution system 122 of computer system 104 may also determine the direction in which the actual location of diffraction spot 116 is displaced from anticipated location 140. The determining of the direction of strain distribution in semiconductor structure 102 may aid strain distribution system 122 of computer system 104 in identifying the approximate location of strain force.

Furthermore, the determining of strain distribution may include determining a force of strain distribution in semiconductor structure 102. That is, strain distribution system 122 of computer system 104 may analyze the determined characteristics of strain distribution to determine an approximate force that may be placed on silicon layer 108 of semiconductor structure 102 during the straining process. More specifically, strain distribution system 122 may analyze: the determined spatial distance (D) between anticipated location 140 and the actual location of a diffraction spot 116 in perimeter tile 160, the direction in which the actual location of diffraction spot 116 is displaced from anticipated location 140 in each perimeter tile 160, and/or the identified approximate location of strain force, to determine an approximate force placed on silicon layer 108 of semiconductor structure 102. By determining the approximate force placed on silicon layer 108 of semiconductor structure 102 during the straining process, strain distribution system 122 may determine if semiconductor structure 102 is susceptible to operational faults or failure. That is, where strain distribution system 122 of computer system 104 determines approximate force causing strain distribution is above a predetermined threshold, computer system 104 may provide an indicator via HMI 138 that the portion of semiconductor 102 depicted in diffraction pattern image 112 may include an undesirable, defective circuit area (e.g., shorted circuit area), which may not allow semiconductor structure 102 to function properly.

Figure 6:
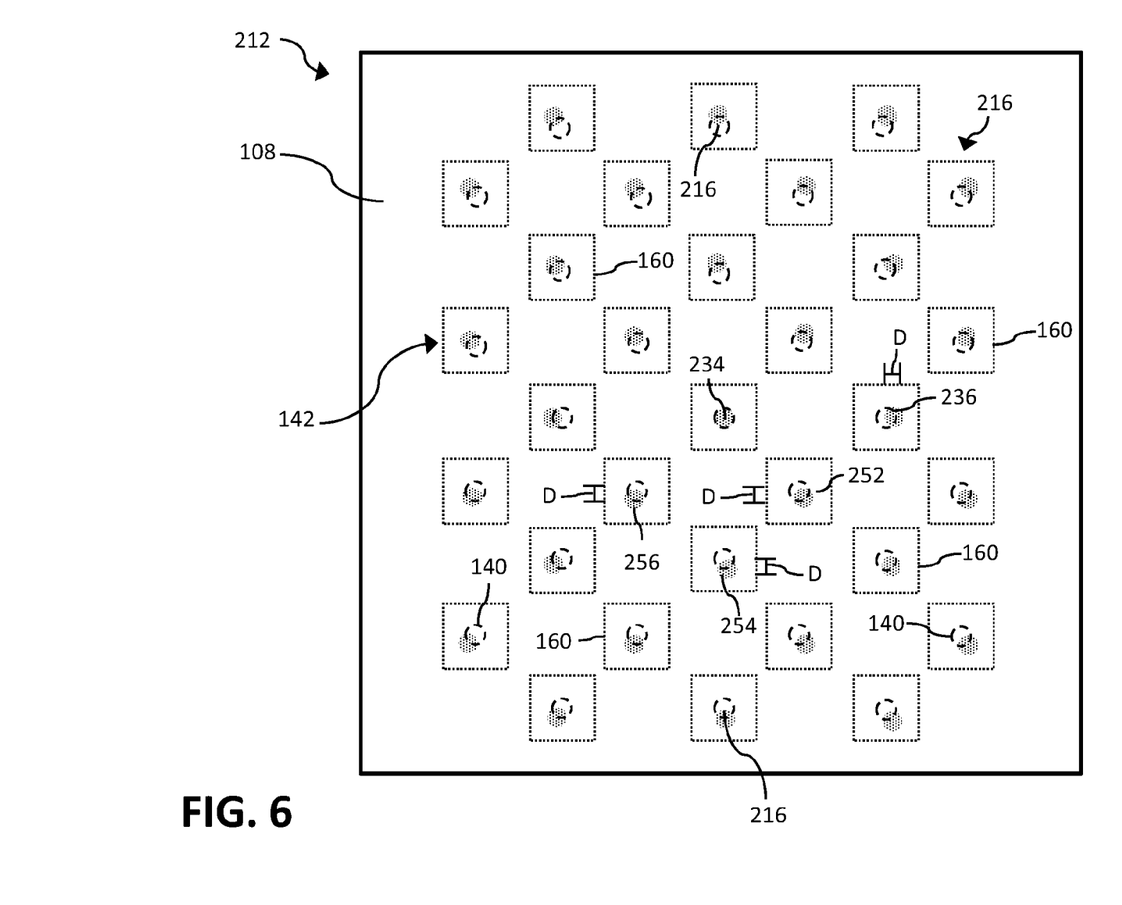
FIG. 6 shows a demonstrative illustration of a diffraction pattern of a portion of a semiconductor structure undergoing a method of analyzing a strain distribution in the semiconductor structure according to additional embodiments of the invention.

Continuing the example of process P106, in process P110 strain distribution system 122 of analyzing system 106 (FIG. 1) may determine the strain distribution (e.g., FIG. 6) within silicon layer 108 of semiconductor structure 102. Turning to FIG. 5, and as discussed herein, strain distribution system 122 of analyzing system 106 (FIG. 1) may determine that the portion of semiconductor structure 102 depicted in diffraction pattern image 112 does not include strain distribution (FIG. 6). More specifically, as discussed herein, the plurality of diffraction spots 116 may be in substantial alignment with the plurality of anticipated locations 140, and may be positioned substantially in the center of the respective perimeter tiles 160. As such, strain distribution system 122 may determine the spatial distance (D) for each of the diffraction spots 116 of diffraction pattern image 112 may equal zero (0). As a result, strain distribution system 122 may determine there is no strain distribution (FIG. 6) in the portion of semiconductor structure 102 depicted in diffraction pattern image 112.

Additionally, it is understood that user 114 may utilize a conventional program stored (not shown) on computer system 104 (FIG. 1) to aid in the identifying the center of first diffraction spot 134, second diffraction spot 136 and/or the plurality of diffraction spots 116. For example, a fitting program (not shown) of computer system 104 may be configured to fit a Gaussian Curve to first diffraction spot 134, second diffraction spot 136 and/or the plurality of diffraction spots 116, to determine the center of each diffraction spot. That is, the fitting program may generate a 2D Gaussian curve of the intensity distribution for each perimeter tiles 160, and may subsequently determine the center of each of the first diffraction spot 134, second diffraction spot 136 and/or the plurality of diffraction spots 116 as the represented peak in the 2D Gaussian curve. As discussed herein, by determining the center of first diffraction spot 134, second diffraction spot 136 and/or the plurality of diffraction spots 116, user 114 may accurately determine the strain distribution in semiconductor structure 102 (FIG. 1).

Turning to FIG. 6, a distinct diffraction pattern image 212 of a distinct portion of semiconductor structure 102 (FIG. 1) is shown. More specifically, diffraction pattern image 212 may represent a diffraction pattern of a distinct portion of semiconductor structure 102, and may include a diffraction pattern distinct from the diffraction pattern depicted in diffraction pattern images 112.

Additionally, as shown in FIG. 6, processes P100-108 may be performed on diffraction pattern image 212 in similar processes as discussed with respect to diffraction pattern image 112. More specifically, locational pattern 142 including anticipated locations 140 and perimeter tiles 160 may be formed and/or generated in diffraction pattern image 212 using similar processes P100-108 as discussed herein with reference to FIGS. 2-4. As shown in FIG. 6, first diffraction spot 234 may be positioned within perimeter tile 160 and in substantially alignment with anticipated location 140. As discussed herein, this may aid in determining the type and/or the amount of strain placed on silicon layer 108 of semiconductor structure 102 (FIG. 1). Additionally, it is understood that locational pattern 142 and perimeter tiles 160 may be formed using the locational pattern 142 and perimeter tiles 160 from diffraction pattern image 112, as shown in FIGS. 3-5. That is, as discussed herein, once a first locational pattern 142 and perimeter tiles 160 are generated, the same pattern may be used through the rest of the diffraction pattern images (e.g., diffraction pattern image 212) of semiconductor structure 102. It is understood that similar components and elements may include similar numbering. As such, redundant explanation of these components and elements are omitted for clarity.

In FIG. 6, diffraction spots 216 of diffraction pattern image 212 may be positioned in a strained pattern or location in silicon layer 108 of semiconductor structure 102 (FIG. 1). More specifically, as shown in FIG. 6, the plurality of diffraction spots 216 may be positioned in a substantially compressive strain pattern, as the plurality of diffraction spots 216 move away from first diffraction spot 234. In an alternative demonstrative illustration, where the plurality of diffraction spots 216 may be positioned in a substantially tensile strain pattern, the plurality of diffraction spots 216 may move toward first diffraction spot 234. As a result of the strained pattern, each the plurality of diffraction spots 216, excluding first diffraction spot 234, may not be in alignment with anticipated locations 140 positioned within diffraction pattern image 212.

As shown in FIGS. 1 and 6, and discussed herein, strain distribution may be determined by strain distribution system 122 (FIG. 1) based on the spatial distance (D) between anticipated location 140 of each diffraction spot 216 and the actual location of each diffraction spot 216 within perimeter tiles 160. More specifically, by determining the spatial distance (D) and the direction of displacement of diffraction spots 216 caused by strain distribution, strain force may be determined. For example, as shown in FIGS. 1 and 6, strain distribution system 122 (FIG. 1) may identify that the plurality of diffraction spots 216 of diffraction pattern image 212 may not be in alignment with anticipated location 140. That is, it may be determined that the spatial distance (D) between anticipated location 140 of diffraction spots 216 in diffraction pattern image 212 and the actual location of diffraction spots 216 in diffraction pattern image 212 is greater than zero (0). As such, strain distribution system 122 (FIG. 1) may further analyze perimeter tiles 160 in diffraction pattern image 212. Strain distribution system 122 may determine spatial distance (D) for all perimeter tiles 160 and may determine the plurality of diffraction spots 216 may be displaced from the strain by a 1% margin. More specifically, as shown in FIG. 6, example diffraction spots 252, 254, 256 of the plurality of diffraction spots 216 may be displaced the spatial distance (D) by 1% from the anticipated location 140, away from first diffraction spot 234. This may determine the approximate straining force that may be applied to silicon layer 108. More specifically, strain distribution system 122 may determine that silicon layer 108 as depicted in diffraction pattern image 212 has undergone a 1% strain.

Furthermore, strain distribution system 122 may determine each of the directions of spatial distance (D) for diffraction spots 216 in diffraction pattern image 212 (e.g., diffraction spots 252, 254, 256). By determining the direction and determining the spatial distance (D) (e.g., straining force), the type of strain (e.g., compressive, tensile) applied to silicon layer 108 may be determined by strain distribution system 122. As shown in FIG. 6, and discussed herein, strain distribution system 122 may determine that the plurality of diffraction spots 216 move 1% from anticipated location 140, and may move substantially away from first diffraction spot 234. As such, strain distribution system 122 may determine that silicon layer 108 of semiconductor structure 108 as depicted by diffraction pattern image 212 has undergone a 1% compressive strain.

As discussed herein, a plurality of diffraction pattern images 112, 212 are used to depict semiconductor structure 102 (FIG. 1). As such, it is understood that processes P100-P110 may be performed continuously for each of the plurality of diffraction pattern images 112, 212 to analyze the strain distribution for the entire semiconductor structure 102. Furthermore, it is understood that each diffraction pattern image 112 may be analyzed individually and sequentially, or may be analyzed concurrently by analyzing system 106.

As discussed herein, computer system 104 (FIG. 1) may implement processes P100-P110 for analyzing strain distribution in semiconductor structure 102. Additionally, it should be understood that processes P100-P110, and specifically, the utilization of perimeter tiles 160 may aid in filtering out undesirable spots (e.g., not diffraction spots 116) that may be captured by TEM 110 when capturing and/or generating diffraction pattern images 112, 212. That is, as discussed herein, perimeter tiles 160 may define a search area in diffraction pattern images 112, 212, and as such, may act as a spatial filter for filtering out spurious spots from other materials that may be included in semiconductor structure 102 (e.g., not silicon layer 108).

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of analyzing a strain distribution in a semiconductor structure, the method comprising:
    determining a crystallographic orientation of a portion of the semiconductor structure depicted in a diffraction pattern image, wherein the diffraction pattern image is captured with a transmission electron microscope (TEM);
    identifying a first diffraction spot and a second diffraction spot in the diffraction pattern image of the portion of the semiconductor structure;
    detecting an anticipated location of each of a plurality of diffraction spots in the diffraction pattern image, based on the identifying of the first diffraction spot, and the second diffraction spot, and the determining of the crystallographic orientation of the portion of the semiconductor structure;
    forming a perimeter tile around the first diffraction spot, the second diffraction spot and the anticipated location of each of the plurality of diffraction spots in the diffraction pattern image;
    storing each of the formed perimeter tiles of the diffraction pattern image; and
    determining the strain distribution in the semiconductor structure based on an actual location of the first diffraction spot, the second diffraction spot and each of the plurality of diffraction spots within the formed perimeter tile, wherein the determining of the strain distribution further includes:
        determining a direction of the strain distribution on the portion of the semiconductor based on a spatial distance between the anticipated location of each of the plurality of diffraction spots and the actual location of each of the plurality of diffraction spots, and
        determining a force of the strain distribution on the portion of the semiconductor based on the spatial distance, the direction of the strain distribution, and an approximate strain location.

2. The method of claim 1, wherein the storing of each of the formed perimeter tiles further comprising storing each of the formed perimeter tiles of the diffraction pattern image on a storage device, separate from storing the entire diffraction pattern image of the portion of the semiconductor structure.

3. The method of claim 1, wherein the perimeter tile includes an area in a spatial range of about 0.5% and about 2.5% of the anticipated location of each of the plurality of diffraction spots.

4. The method of claim 1, wherein the actual location of each of the plurality of diffraction spots is within a spatial range of about 0% to about 2% of the anticipated location of each of the plurality of diffraction spots.

5. The method of claim 1, wherein the detecting of the anticipated location of each of the plurality of diffraction spots includes identifying a locational pattern based upon a spatial difference between the first diffraction spot and the second diffraction spot.

6. The method of claim 1, wherein the determining of the strain distribution further comprises measuring the spatial distance between the anticipated location of each of the plurality of diffraction spots and the actual location of each of the plurality of diffraction spots within the diffraction pattern image.

7. A computer system comprising:
    at least one computing device configured to analyze a strain distribution in a semiconductor structure by performing actions including:
        determining a crystallographic orientation of a portion of the semiconductor structure depicted in a diffraction pattern image, wherein the diffraction pattern image is captured with a transmission electron microscope (TEM);

identifying a first diffraction spot and a second diffraction spot in the diffraction pattern image of the portion of the semiconductor structure, based on the determined crystallographic orientation of the portion of the semiconductor structure;

detecting an anticipated location of each of a plurality of diffraction spots in the diffraction pattern image, based on the identifying of the first diffraction spot, and the second diffraction spot, and the determining of the crystallographic orientation of the portion of the semiconductor structure;

forming a perimeter tile around the first diffraction spot, the second diffraction spot and the anticipated location of each of the plurality of diffraction spots in the diffraction pattern image; and determining the strain distribution in the semiconductor structure based on an actual location of the first diffraction spot, the second diffraction spot and each of the plurality of diffraction spots within the formed perimeter tile, wherein the determining of the strain distribution further includes:

determining a direction of the strain distribution on the portion of the semiconductor based on a spatial distance between the anticipated location of each of the plurality of diffraction spots and the actual location of each of the plurality of diffraction spots, and determining a force of the strain distribution on the portion of the semiconductor based on the spatial distance, the direction of the strain distribution, and an approximate strain location.

8. The computer system of claim 7, wherein the at least one computing device configured to analyze the strain distribution in the semiconductor structure performs further actions including: storing each of the formed perimeter tiles of the diffraction pattern image on a storage device, separate from storing the entire diffraction pattern image of the portion of the semiconductor structure.

9. The computer system of claim 7, wherein the perimeter tile includes an area in a spatial range of about 0.5% and about 2.5% of the anticipated location of each of the plurality of diffraction spots.

10. The computer system of claim 7, wherein the actual location of each of the plurality of diffraction spots is within a spatial range of about 0% to about 2% of the anticipated location of each of the plurality of diffraction spots.

11. The computer system of claim 7, wherein the detecting of the anticipated location of each of the plurality of diffraction spots includes identifying a locational pattern based upon a spatial difference between the first diffraction spot and the second diffraction spot.

12. The computer system of claim 7, wherein the determining of the strain distribution further comprises measuring the spatial distance between the anticipated location of each of the plurality of diffraction spots and the actual location of each of the plurality of diffraction spots within the diffraction pattern image.

13. A computer program product stored on a non-transitory computer-readable storage medium and having program code for analyzing a strain distribution in a semiconductor structure, the program code executable by at least one computer system to perform a method comprising:

determining a crystallographic orientation of a portion of the semiconductor structure depicted in a diffraction pattern image, wherein the diffraction pattern image is captured with a transmission electron microscope (TEM);

identifying a first diffraction spot and a second diffraction spot in the diffraction pattern image of the portion of the semiconductor structure, based on the determined crystallographic orientation of the portion of the semiconductor structure;

detecting an anticipated location of each of a plurality of diffraction spots in the diffraction pattern image, based on the identifying of the first diffraction spot, and the second diffraction spot, and the determining of the crystallographic orientation of the portion of the semiconductor structure;

providing a perimeter tile around the first diffraction spot, the second diffraction spot and the anticipated location of each of the plurality of diffraction spots in the diffraction pattern image; and determining the strain distribution in the semiconductor structure based on an actual location of the first diffraction spot, the second diffraction spot and each of the plurality of diffraction spots within the formed perimeter tile, wherein the determining of the strain distribution further includes:

determining a direction of the strain distribution on the portion of the semiconductor based on a spatial distance between the anticipated location of each of the plurality of diffraction spots and the actual location of each of the plurality of diffraction spots, and determining a force of the strain distribution on the portion of the semiconductor based on the spatial distance, the direction of the strain distribution, and an approximate strain location.

14. The computer program of claim 13, wherein the method performed by the at least one computer system further comprises: storing each of the formed perimeter tiles of the diffraction pattern image on a storage device, separate from storing the entire diffraction pattern image of the portion of the semiconductor structure.

15. The computer program of claim 13, wherein the actual location of each of the plurality of diffraction spots is within a spatial range of about 0% to about 2% of the anticipated location of each of the plurality of diffraction spots.

16. The computer program of claim 13, wherein the detecting of the anticipated location of each of the plurality of diffraction spots includes identifying a locational pattern based upon a spatial difference between the first diffraction spot and the second diffraction spot.

17. The computer program of claim 13, wherein the determining of the strain distribution further comprises measuring the spatial distance between the anticipated location of each of the plurality of diffraction spots and the actual location of each of the plurality of diffraction spots within the diffraction pattern.

18. The computer program of claim 13, wherein the determining of the strain distribution further comprises:

determining a direction of the strain distribution on the portion of the semiconductor; and determining a force of the strain distribution on the portion of the semiconductor.

* * * * *